United States Patent [19]
Grimson et al.

[11] Patent Number: 5,999,840
[45] Date of Patent: Dec. 7, 1999

[54] SYSTEM AND METHOD OF REGISTRATION OF THREE-DIMENSIONAL DATA SETS

[75] Inventors: W. Eric L. Grimson, Lexington; Steven J. White, Boston; Gil J. Ettinger, Lexington; William M. Wells, III, Cambridge; Tomas Lozano-Pérez, West Newton; Ronald Kikinis, Brookline, all of Mass.

[73] Assignee: Massachusetts Institute of Technology, Cambridge, Mass.

[21] Appl. No.: 08/521,018

[22] Filed: Aug. 30, 1995

Related U.S. Application Data

[63] Continuation-in-part of application No. 08/299,378, Sep. 1, 1994, Pat. No. 5,531,520.

[51] Int. Cl.[6] .......................................................... A61B 5/05
[52] U.S. Cl. .......................................... 600/424; 606/130
[58] Field of Search .................... 128/653.1; 364/413.13, 364/413.14, 413.19; 606/130; 382/161, 154, 294, 293, 100, 318; 348/77; 600/407, 424

[56] References Cited

U.S. PATENT DOCUMENTS

| | | | |
|---|---|---|---|
| 4,395,731 | 7/1983 | Schoolman | 358/88 |
| 4,498,778 | 2/1985 | White . | |
| 4,628,469 | 12/1986 | White . | |
| 4,679,076 | 7/1987 | Vikterlöf . | |
| 4,705,401 | 11/1987 | Addleman et al. . | |
| 4,737,032 | 4/1988 | Addleman et al. . | |
| 4,846,577 | 7/1989 | Grindon . | |
| 4,853,777 | 8/1989 | Hupp . | |
| 5,095,887 | 3/1992 | Leon et al. | 359/375 |
| 5,099,846 | 3/1992 | Hardy . | |
| 5,261,404 | 11/1993 | Mick et al. . | |
| 5,376,796 | 12/1994 | Chan et al. . | |
| 5,446,548 | 8/1995 | Gerg et al. | 128/653.1 |
| 5,447,154 | 9/1995 | Cinquin et al. | 128/653.1 |
| 5,531,520 | 7/1996 | Grimson et al. . | |
| 5,740,802 | 4/1998 | Nafis et al. . | |

FOREIGN PATENT DOCUMENTS

| | | |
|---|---|---|
| 43 04 571 | 8/1994 | Germany . |
| 63-501526 | 6/1988 | Japan . |
| 4-61848 | 2/1992 | Japan . |
| 4-76788 | 3/1992 | Japan . |
| 7-508449 | 9/1995 | Japan . |
| 2250164 | 5/1992 | United Kingdom . |
| WO 87/01194 | 2/1987 | WIPO . |
| WO 94/24631 | 10/1994 | WIPO . |

OTHER PUBLICATIONS

Proc. 2nd IEEE Workshop of Applications of Computer Vision, pp. 240–248, Dec. 5–7, 1994, by P. Hemler et al. "Frameless registration of MR and CT 3D volumetric data sets".

Proc. 5th Annual IEEE Symposium on Computer–Based Medical Systems, pp. 309–314, Jun. 14–17, 1992, by P. Hemler et al., "A Three Dimensional Guidance System for Frameless Sterotatic Neurosurgery".

IEEE Computer Society Press—Computers In Cardiology, pp. 509–512, Sep. 23–26, 1991, by J. Snoeck et al., "The DSI Technique Used on DDD Paced Patients".

(List continued on next page.)

Primary Examiner—Brian Casler
Attorney, Agent, or Firm—Samuels, Gauthier, & Stevens

[57] ABSTRACT

An image data registration system and method of storing a first data set of three-dimensional image data associated with a predetermined portion of an object with reference to a first coordinate frame; obtaining and storing a second data set of three-dimensional image data associated with a surface of the predetermined portion of the object with reference to a second coordinate frame; obtaining and storing a third data set of three-dimensional image data associated with a probe in the vicinity of the predetermined portion of the object with reference to a third coordinate frame; and registering the first, second and third data sets to generate a matched image data set in which the first, second and third coordinate frames are relatively aligned with one another.

39 Claims, 7 Drawing Sheets

OTHER PUBLICATIONS

Chen, George T.Y., and Charles A. Pelizzari, "Image Correlation Techniques in Radiation Therapy Treatment Planning", *Computerized Medical Imaging and Graphics*, vol. 13, No. 3, May–Jun. 1989, pp. 235–240.

Grimson, W. Eric L., *Object Recognition by Computer: The Role of Geometric Constraints*, The MIT Press, 1990, cover pages and pp. 47–57.

Grimson, E., T. Lozano–Pérez, W. Wells, G. Ettinger, S. White and R. Kikinis, "Automated Registration for Enhanced Reality Visualization in Surgery", *AAAI Symposium Series: Applications of Computer Vision in Medical Image Processing*, Mar. 21–23, 1994, pp. 26–29.

Huttenlocher, Daniel P., and Shimon Ullman, "Recognizing Solid Objects by Alignment with an Image", *International Journal of Computer Vision*, 5:2, 1990, pp. 195–212.

Lavallee, S., L. Brunie, B. Mazier, and P. Cinquin, "Matching of Medical Images for Computed and Robot Assisted Surgery", *Annual International Conference of the IEEE Engineering in Medicine and Biology Society*, vol. 13, No. 1, 1991, pp. 0039–0040.

Lavallée, Stéphane, Richard Szeliski, and Lionel Brunie, "Matching 3–D Smooth Surfaces with their 2–D Projections Using 3–D Distance Maps", *Geometric Methods in Computer Vision*, vol. 1570, Jul. 25–26, 1991, pp. 1–15.

Levin, David N., Xiaoping Hu, Kim K. Tan, Simranjit Galhotra, Charles A. Pelizzari, George T.Y. Chen, Robert N. Beck, Chin–Tu Chen, Malcolm D. Cooper, John F. Mullan, Javad Hekmatpanah, and Jean–Paul Spire, "The Brain: Integrated Three–dimensional Display of MR and PET Images", *Radiology*, vol. 172, No. 3, Sep. 1989, pp. 783–789.

Press, William H., Saul A. Teukolsky, William T. Vetterling, and Brian P. Flannery, *Numerical Recipes in C: The Art of Scientific Computing*, second edition, Cambridge University Press, cover page and pp. 412–420.

SYSTEM AND METHOD OF REGISTRATION OF THREE-DIMENSIONAL DATA SETS

This is a continuation-in-part of application Ser. No. 08/299,378 filed on Sep. 1, 1994 now U.S. Pat. No. 5,531,520.

This invention was made with government support under Grant Number N00014-91-J-4038 awarded by the Navy. The government has certain rights in the invention.

The invention relates in general to a system and method of image data registration, and more particularly to a system and method of registering three-dimensional surgical image data utilized in image guided surgery and frameless stereotaxy.

Neurosurgical procedures, such as biopsy or tumor extraction, require highly precise localization on the part of the surgeon, in order to attain the desired extraction of material while minimizing collateral damage to adjacent structures. The problem is exacerbated by the fact that the localization is three dimensional in nature, and often requires localizing a structure deeply buried within the cranium. While methods exist (e.g. MRI, CT) for imaging and displaying the 3D structure of the cortex, this still leaves the surgeon with the problem of relating what she sees on the 3D display with the actual anatomy of the patient.

Conventional solutions typically involve presurgically attaching a stereotactic frame to the patient's skull, then imaging the skull and frame as a unit. This allows the surgeon to locate, from the 3D images, the location of the tumor or other target relative to a coordinate system attached to the stereotactic frame, and thus to the patient's head. As well, the frame typically includes a movable armature that allows the positioning of a probe at any orientation relative to the patient. This lets the surgeon mark a planned angle of entry to access the tumor, thus localizing the expected extraction of material.

Unfortunately, the use of stereotactic frames is both cumbersome to the surgeon, and involves considerable discomfort to the patient, who must wear the device for several days between imaging and surgery. In addition, such frames can have limited flexibility, especially should surgical plans have to change in the middle of the procedure, e.g. if the line of attack is found to pass through critical regions, such as the motor strip.

In addition to the aforementioned drawbacks of conventional surgical techniques, it is often necessary for surgeons to insert rigid probes or instruments into bodily cavities for certain procedures. Typically, such insertions are required for removal of material from the interior structure of the patient, without the need for extensive surgical invasion of the patient. Unfortunately, it is difficult to view the probe with respect to the internal parts of the cavity in which the instrument is inserted.

Accordingly, it is an object of the present invention to provide an imaging method and system which registers sets of three-dimensional image data of an object.

It is another object of the present invention to provide a surgical imaging method and system which registers clinical data, such as segmented MRI or CT reconstructions, with surface data associated with a portion of a patient's body.

It is yet another object of the present invention to provide a surgical imaging method and system which generates real-time, adaptive, enhanced visualizations of the patient in the operating room so as to accommodate dynamic image-guided surgical planning and image guided surgical procedures, such as biopsies or minimally invasive therapeutic procedures.

It is still another object of the present invention to provide a surgical imaging method and system which establishes visual feedback to the surgeon to accommodate viewing the position of the instrument in the patient, thus enhancing the ability to guide further insertions and procedures with the rigid instrument.

SUMMARY OF THE INVENTION

The present invention provides an image data registration system and method of storing a first data set of three-dimensional image data associated with a predetermined portion of an object as model image data with reference to a first coordinate frame; obtaining and storing a second data set of three-dimensional surface image data associated with a surface of the predetermined portion of the object with reference to a second coordinate frame; obtaining and storing a third data set of three-dimensional probe image data associated with a probe in the vicinity of the predetermined portion of the object with reference to a third coordinate frame; and registering the first, second and third data sets to generate a matched image data set in which the first, second and third coordinate frames are relatively aligned with one another.

The present invention more particularly provides a surgical method and system which performs the registration of clinical sensory data with the corresponding position of the patient's body on the operating table at the time of surgery, and with surgical instruments, using methods from visual object recognition, which do not require the use of a previously attached stereotactic frame. The method has been combined with an enhanced visualization technique, in which there is displayed a composite image of the 3D anatomical structures and probes with a view of the patient's body.

This registration enables the transfer to the operating room of preoperative surgical plans, obtained through analysis of the segmented 3D preoperative data, where they can be graphically overlaid onto video images of the patient. Such transfer allows the surgeon to apply carefully considered surgical plans to the current situation and to mark landmarks used to guide the progression of the surgery. Extensions of the method and system include adaptively re-registering the video image of the patient to the 3D anatomical data, as the patient moves, or as the video source moves.

The file of this patent contains at least one drawing executed in color. Copies of this patent with color drawing(s) will be provided by the Patent and Trademark Office upon request and payment of the necessary fee.

DETAILED DESCRIPTION OF THE ILLUSTRATED EMBODIMENTS

For purposes of illustration, an exemplary embodiment of the present invention will be described with reference to a craniotonomy procedure. It will be appreciated that the described image registration method and system of the present invention is not limited to use only with cranial structures, but in fact may be used for registering three-dimensional image data for sets of other objects including other portions of an anatomical body.

Figure 1:
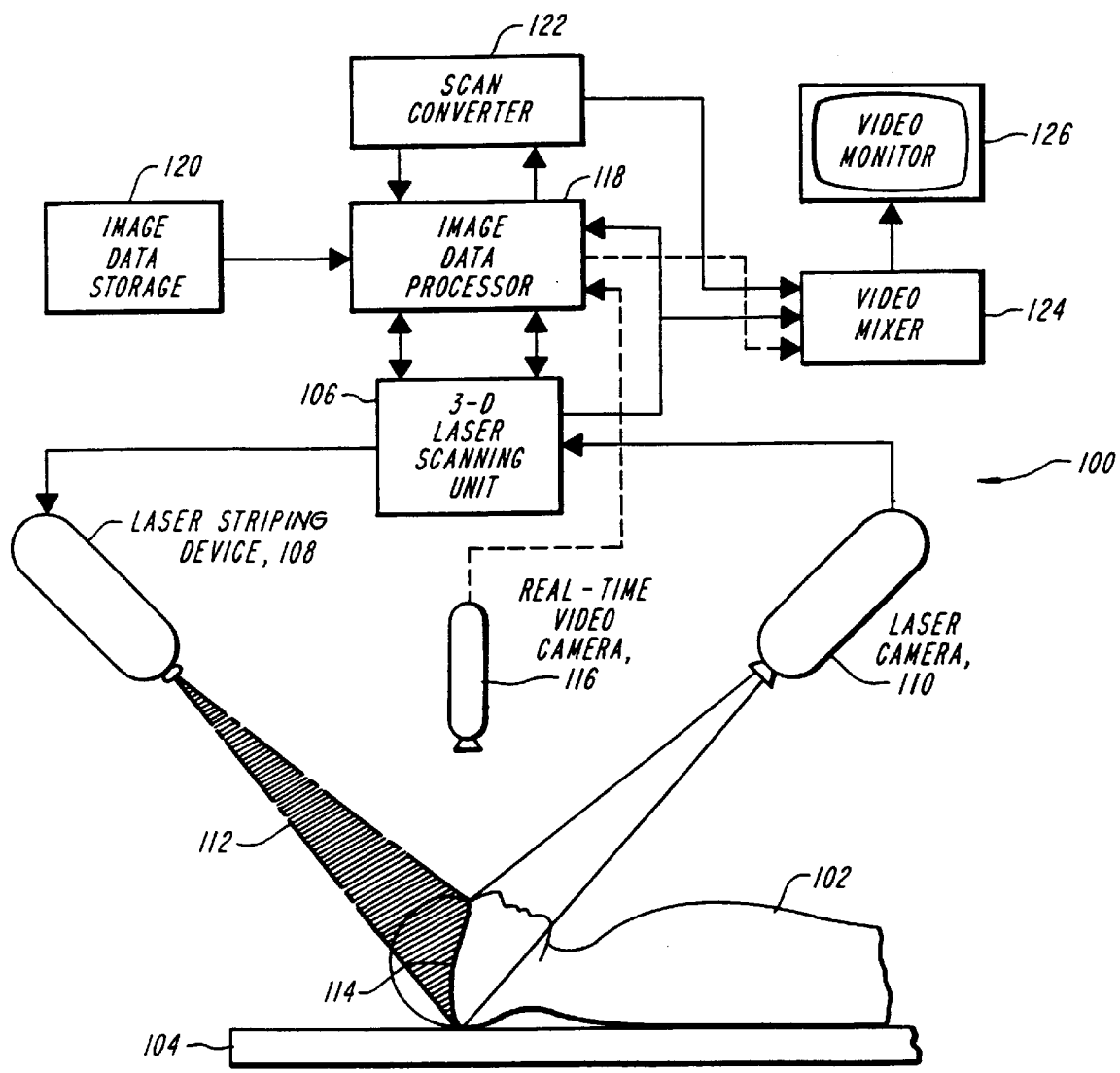
FIG. 1 shows a block diagram of an image data registration system in accordance with the present invention.

Accordingly, with reference to FIG. 1, there is shown an image data registration system 100 in accordance with the present invention. The system 100 operates in accordance with the following exemplary overview for cranial surgery. A patient requiring surgical therapy is initially scanned by a three-dimensional, high resolution, internal anatomy scanner, such as Magnetic Resonance Imaging (MRI) or Computed Tomography (CT). It will be appreciated that any form of volumetric imaging techniques, such as PET, SPECT, etc., can also be used. If a brain atlas is available, or if a previous, segmented scan of the patient is available, the current scan is registered to this prior scan, and the match is used to drive fast, accurate, automated segmentation of the current scan, and to identify changes since the reference scan was taken, to better identify the pathology. If no previous information is available, then the current scan is segmented to produce organ surface data and other anatomical structures such as ventricles and tumor tissue using conventional automated algorithms. This is typically done by training an intensity classifier on a user selected set of tissue samples, where the operator uses knowledge of anatomy to identify the tissue type. Once initial training is completed, the rest of the scans can be automatically classified on the basis of intensities in the scanned images, and thus segmented into tissue types. Conventional automatic methods for removing gain artifacts from the sensor data can be used to improve the segmentation. This 3D anatomical reconstruction is referred to as the model, and is represented relative to a model coordinate frame. For simplicity, the center of the coordinate system can be taken as the centroid of the points.

The patient is then placed in an operating room, which is equipped with a laser range scanner for obtaining depth data of the patient's skin surface where the surgery is to be performed; and enhanced visualization equipment, such as a video or digital camera, mixer and display monitor, a head-mounted display with trackable landmarks, an operating room microscope with video projection overlay feed, along with microscope-mounted trackable landmarks, or transparent projection screens along with screen mounted trackable landmarks, medical instrument holders containing trackable landmarks. The operating table may also contain fixed raised landmarks that will remain viewable and in the same position during surgery, and landmark tracking equipment.

Prior to draping, the patient is scanned by the laser range scanner. The 3D locations of any table landmarks are also calculated to identify their location relative to the patient. The current MRI or CT scan is automatically registered to the patient skin surface depth data obtained by the laser range scanner. This provides a transformation from MRI/CT to patient. The position and orientation of a video camera relative to the patient is determined by matching video images of the laser points on an object to the actual 3D laser data. This provides a transformation from patient to video camera. The registered anatomy data is displayed in enhanced visualization to "see" inside the patient. In particular, the two previously computed transformations can be used to transform the 3D model into the same view as the video image of the patient, so that video mixing allows the surgeon to see both images simultaneously. Alternatively, the images are combined with a surgical microscope or transparent imaging panel in order to augment the line-of-sight view of the surgeon with the MRI data. The patient is draped and surgery is performed.

The enhanced visualization does not interfere with the surgeon, nor does it require any procedures different from that to which the surgeon is accustomed. Rather, the system provides the surgeon with additional visualization information to greatly expand the limited field of view. The location of table landmarks can be continually tracked to identify changes in the position and attitude of the patient's head, relative to the visualization camera. Visualization updates are performed by re-rendering based on this tracking. Viewer location is continually tracked to identify any changes in the position of the viewer. In the case of a stationary video camera, this is unnecessary, though in the case of head-mounted displays such tracking is necessary. Visualization updates are performed by re-registration. If landmarks are used for tracking, re-registration is unnecessary. Updates are performed simply by re-rendering based on the tracked position information. Medical instruments may be tracked to align them with predetermined locations as displayed in the enhanced visualization. In general, the surgical procedure is executed with an accurately registered enhanced visualization of the entire relevant anatomy of the patient, and thus with reduced side effects.

With reference back to FIG. 1, the patient's body 102 is positioned on the operating table 104. The system 100 obtains three-dimensional image data from the skin surface of the patient with the utilization of a 3D laser scanning unit 106, which includes both a laser striping device 108 and a laser camera 110. Exemplary apparatus for carrying out the laser striping is described in U.S. Pat. Nos. 4,498,778 and 4,628,469, incorporated herein by reference. In essence, the system utilizes uses a plane of laser light and a video camera to obtain three dimensional measurements of the patient's skin, and uses the "structured light" method of obtaining the desired measurements. This method is based on the principal of triangulation for measurement.

The 3D laser scanning unit 106 controls the laser striping device 108 to generate a laser beam which is optically spread out to form a plane of light 112, which is projected in front of the laser camera 110 at an angle to the optical axis of the camera. The plane of light is formed, for example, by a laser beam reflected off of an oscillating mirror or a passive lens as is well known.

The laser camera 110 is placed at an angle to the plane of light such that a portion of the plane is in the camera field of view (FOV). As this plane of light strikes an object, such as the patient's skin, the diffuse reflection appears on the video camera image as a line of light 114. In other words, when an object is placed in this visible region such that it intersects the laser plane, points in the camera image plane illuminated by the laser unambiguously correspond to fixed 3D scene points. This is most easily appreciated by considering the case of objects on a flat support plane, with the plane of laser light striking the support plane at an oblique angle. When only the support plane is imaged, the laser plane makes a straight line in the image, and the camera can be oriented so that this line is vertical, for example. When an object is placed on the support plane, the imaged intersection of laser plane and the object is deflected from the previously recorded position, by an amount that is a direct function of the height of the object above the plane. By measuring this deflection, the distance to the observed point can be computed.

The projection of the stripe in the plane of the illumination onto the focal plane of the imaging device is unique. Each sample point in the image plane corresponds to a unique point in the plane of the laser illumination. This correspondence can be determined through a transform which, in turn, can be determined by scanning a known 3D shape. The laser scanning unit uses this unique mapping between image plane points and 3D points in space to determine the 3D coordinates points on the surface of the patient's skin illuminated by the laser. When the laser is moved, a different cross-section of the skin under the scanner can be measured. With multiple scans and the acquisition of multiple points within each scan, a sample grid is converted into 3D measurements. The density is only limited by the number of scans taken and the number of samples in each scan taken from the scanning unit. In the surgery example, approximately 20 scans are taken with between 100 and 200 3D points measured in each.

The laser scanning unit 106 used could be substituted for by any of a number of surface 3D scanners. There are numerous other conventional methods, including laser radar and moire fringe analysis, that could be used in the system 100. Other non-contact sensor types, including ultrasound or radar, are possible, as are a wide array of contact (probing) types of measurement devices. All that is required is the derivation of a modest number of accurate skin surface 3D points.

The system 100 also includes a real-time video camera 116 for providing a real-time image of the patient to which the 3D anatomy data will be registered. In one embodiment, the real-time video camera may be the same camera as the laser camera 110. An image data processor 118 serves to register the 3D surface data to the 3D anatomy data which has been prestored in an image data storage unit 120. A scan converter 122 is used to take the terminal outputs of the processor and convert them into video signals. Some computer processors provide direct video outputs, and thereby wouldn't require a scan converter. In an exemplary embodiment, the image data processor is an IBM RS6000 or IBM PVS used in conjunction with a Sun Sparc 10. A video mixer 124 mixes the video images from the processor, scanning unit and real-time video camera and thereafter fed to a video monitor 126 for live video visualizations enhanced with conventional computer graphics.

Prior to using the aforementioned hardware in a surgical setting, a calibration of the system is desirable. Calibration of the laser scanning unit 106 including the laser striping unit 108 and the cameras 110, 116 is performed using scan data from a precisely machined shape referred to as a gauge. This known shape, along with the images of the laser scans from it, can be used to precisely calibrate the laser instrument such that all subsequent measurements, anywhere in the operating range of the scanning unit will result in accurate 3D measurements as measured relative to some fixed reference frame. Since this reference frame is arbitrary, vertices of the laser system calibration gauge are used to define the frame.

The real-time video camera is also calibrated using the same gauge. The camera calibration is used to determine the appropriate viewpoint for rendering the registered 3D images prior to being mixed with the video images. The calibration determines the focal length of the camera lens, the position of the focal point, and the orientation of the image plane relative to the 3D laser reference frame. Since the laser calibration provides a mapping between every 2D point on the image plane and their corresponding 3D point on the laser plane, each measurement from objects in front of the scanning unit provides such a image/laser plane point correspondence and can be used to find the camera model.

In the case where the laser camera is used as the real-time video camera, since it is fixed relative to the scanner, an initial estimate of the camera position is based on the geometry of the setup. The calibration involves the following steps: 1) project the measured 3 D points onto the image plane using the latest estimate of the camera model; 2) determine the summation of squared distances between each 2D projection from the previous step and the known 2D image points using the laser measurements; and 3) modify the camera model, preferably using the conventionally known Powell's method, described by Press et al., *Numerical Recipes in C, The Art of Scientific Computing*, Second Edition, Cambridge University Press, 1992, incorporated herein by reference, to minimize the error measure from step 2. Once the camera model has been adjusted to minimize the reprojection error until the aggregate error is less than some predefined threshold, the camera calibration is complete.

Figure 2:
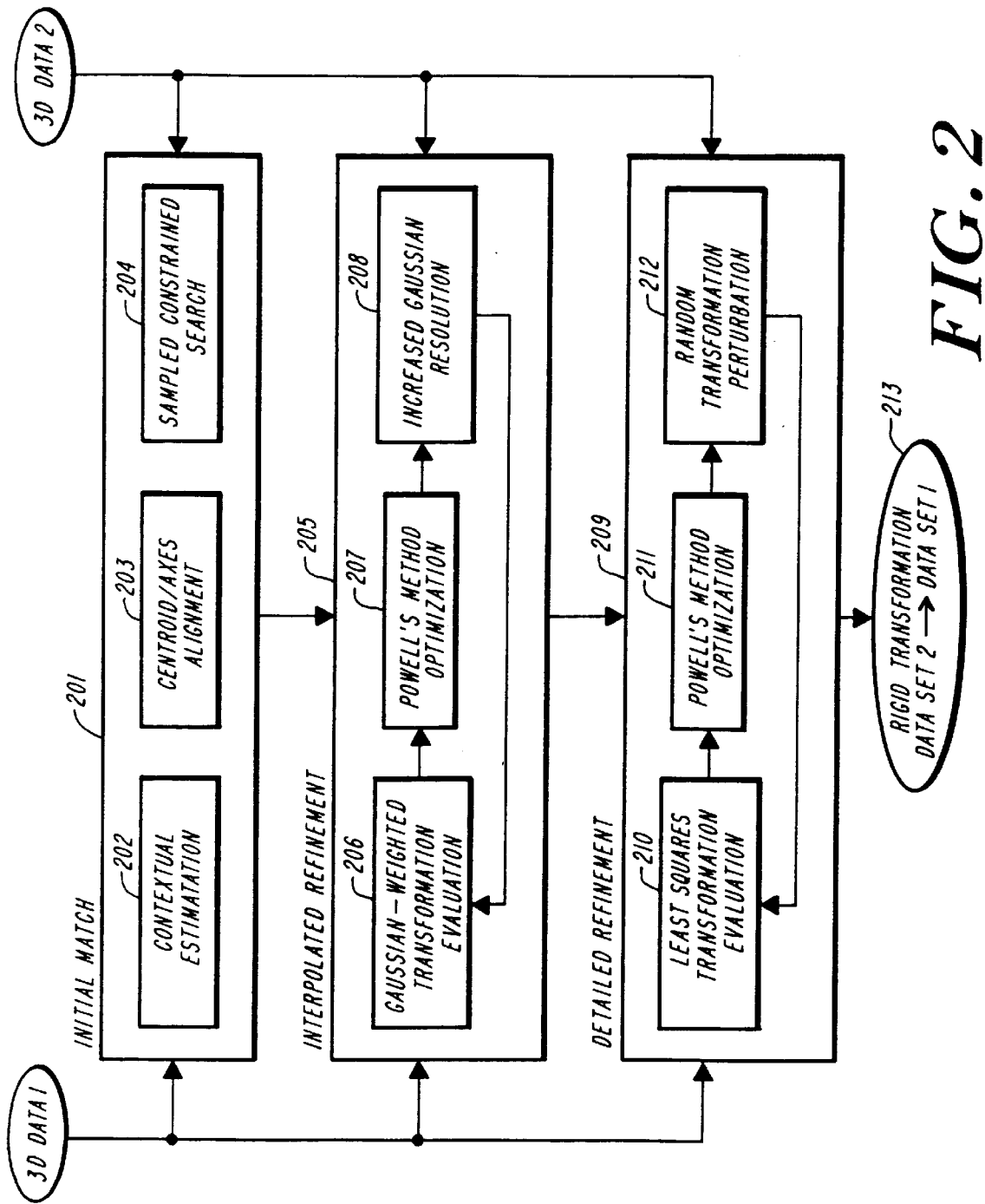
FIG. 2 shows a flow outline of the data registration technique utilized in accordance with the present invention.

The data registration technique utilized in accordance with the present invention is described hereinafter with reference to the flow outline of FIG. 2. The rigid 3D—3D registration technique in its general form consists of the following input and output. The input comprises two 3D surface data sets, represented as sets of 3D points, each in its own coordinate frame. In the illustrated exemplary embodiment, one of these data sets would be from the laser scanner, and the other would be from a segmented skin surface of a medical scan, such as CT or MRI. other embodiments , not relying on the laser scanner, are possible, however, and are described below. The points are assumed to lie on the same structural surface, although the coverages of the points do not need to exactly overlap and outliers may be present. The output involves a six degree-of-freedom rigid body transformation mapping one of the data sets into the other, or equivalently, transforming the coordinate frame of one data set into the other. Such six degree-of-freedom methods solve for three translation and three rotation parameters for matching the two data sets. The method is based on a hierarchical solution approach in which coarse initial alignments are generated using coarse resolution data and then refined using a series of optimization steps to guide the solution towards the best match.

Although the system 100 will operate without such information, it is convenient to specify a body axis and a nose axis, both in model coordinates, and in laser coordinates. Typically an axis from the center of the head through the top of the skull is taken as the body axis, and an axis from the center of the head through the nose is taken as the nose axis. All of the axes need only be roughly accurate. The model axes should be given in terms of model coordinates, and the data axes should be provide in terms of laser coordinates. Accordingly, the operator can perform an initial coarse alignment of the data. This initial alignment does not need to be highly accurate. Rotational errors on the order of 10–20 degrees and translational errors on the order of centimeters are permissible.

In the initial data matching method of the registration process (step 201), the image data processor 118 operates to generate a coarse alignment of the two 3D data sets to use as a starting point for subsequent refinement. The data matching method utilizes several stage approaches for accomplishing the initial match, including contextual estimation (step 202), centroid/axes alignment (step 203), and sampled constrained search (step 204).

The contextual estimation stage relies on an operator's knowledge of the rough pose of patient with respect to the scanner and the operating room for use to estimate an alignment. If rough body and nose axes estimates are known, the operator can use these together with knowledge of the view direction of the laser camera 110 to estimate a rough view direction of the model or object being observed. One such method involves the user specifying a rough view (e.g. right side up, left side up, etc.) and then specifying a rough orientation, in that view, of the nose and/or body axis. This can be used to compute an initial alignment of the body relative to the MRI or CT data.

In an exemplary case, given the rough view, a sampled set of visible points of the laser line 114 is extracted using a z-buffer. In particular, given a pixel size for the z-buffer and given an orientation for that buffer, a projection of all of the model points into this array is made. Within each pixel, only the point closest to the viewer is kept. This action provides a temporary model, which can be used for matching. It will be appreciated that even if body and nose axes estimates are available, they are usually not sufficiently accurate to define the final solution.

If estimates of the axes are not available to the operator, then a sample of a set of views of the model is taken, by sampling a set of evenly spaced directions on the view sphere. For each view, the z-buffer method described above is used to extract a sampled set of visible points of the model.

Thereafter, a graphical interface with the image data processor is used which enables the operator to guide the two data sets into rough initial alignment. In the exemplary embodiment, the interface provides the operator with two stages for alignment. The first stage presents an image of the patient as seen from the laser camera 110 on top of which is superimposed the positions of the laser data points, as seen in that view. The operator employs a conventional computer mouse, for example, to delineate those laser points that are to be included as part of the data set. This is done, for example, by drawing bounding boxes around the sets of points to be included.

Once the data has been selected, a second graphical interface presents three orthogonal views of the anatomical 3D data set, for example the 3D MRI data, together with the selected laser data points on the video monitor 126. The operator can again edit the laser points, in this case using bounding boxes to indicate points to be excluded from the data set. Once the data has been filtered in this way, the computer mouse is employed to manipulate the laser data relative to the anatomical 3D data. In particular, the interface is used to translate (in 3D) the laser data relative to the MRI data, and to rotate the laser data about any of the three axes of the orthogonal views. The result of these operations is that the laser data may be translated and rotated arbitrarily in order to bring the two data sets into rough alignment. The output of the stage, upon completion, is a rough six-degree-of-freedom transformation of one data set into the other.

With respect to the centroid/axes alignment stage, if the two data sets (almost) completely overlap each other, a method is used to align the data sets by first translating the second data set so that its centroid aligns with the centroid of the first data set. Then the second data set is rotated so that its principal directions (moments of inertia) align with the principal directions of the first data set. These directions are computed by taking the eigenvectors of the inertia matrix of each data set.

In the sampled constrained search stage, if there is limited overlap in the coverage of the two data sets (i.e., if there are not both relatively complete models of the anatomy), a sample is taken of a small number (e.g. three) of widely spaced points from one of the data sets, and then using an interpretation tree search as described in Grimson, *Object Recognition by Computer: The Role of Geometric Constraints*, MIT Press, 1990, incorporated herein by reference, those sampled points are matched to data points in the other data set. The interpretation tree search method basically searches over all possible ways of matching small sets of data features from the two data sets. For each pairing of data features from the two data sets, the method tests whether the pairwise distances between points are roughly the same. If all such tests are valid, the match is kept, and the coordinate frame transformation that maps the data points from the first set into their corresponding points in the second set is computed.

The described transformations form a set of hypotheses. Due to the sampling of the data, the actual corresponding points may not exist, thus the hypothesized transformations are at best approximations to the actual transformation. An alignment method, as described in Huttenlocher et al., *Recognizing Solid Objects by Alignment With an Image*, International Journal Computer Vision, 5 (2), 1992, pp. 195–212, incorporated herein by reference, is used to filter these hypotheses. Accordingly, for each hypothesis, a verification is made that the fraction of the laser points, transformed by the hypothesized transformation, without a corresponding model point within some predefined distance is less than some predefined bound. Those hypotheses that fail this verification are discarded. For efficiency, two levels of sampling of the laser points are used, first verifying that a coarsely sampled set of laser points are in agreement, then further verifying, for those that pass this test, that all the laser points are in agreement.

The image data processor next operates to perform an interpolated refinement method (step 205) which includes the stages of Gaussian-weighted transformation evaluation (step 206), Powell's method of optimization (step 207), and increased Gaussian resolution (step 208).

For each verified hypothesis, the image data processor performs an initial refinement aimed at guiding the registration in the general direction of the global error minimum. To perform this refinement an evaluation is made of the current pose by summing, for all transformed points (from data set 2), a term that is itself a sum of the distances from the transformed point to all nearby reference surface points (data set 1), where the distance is weighted by a Gaussian distribution. This Gaussian weighted distribution is a method for roughly interpolating between the sampled reference points to estimate the nearest point on the underlying surface to the transformed data point. More precisely, if $l_i$ is a vector representing a data point, $m_j$ is a vector representing a reference point, and T is a coordinate frame transformation, then the evaluation function for a particular pose (or transformation) is shown in the following equation:

$$E_1(T) = -\sum_i \sum_j e - \frac{|Tl_i - m_j|^2}{2\sigma^2} \qquad (1)$$

This objective function can be visualized as if a Gaussian distribution of some spread a is placed at each reference surface point, then summed with the contributions from each such distribution at each point in the volume. The contribution of each transformed data point towards the evaluation function is simply the summed value at that point. Because of its formulation, the objective function is generally quite smooth, and thus facilitates pulling in solutions from moderately removed locations in parameter space. This evaluation function is iteratively minimized using the conventionally known Powell's method, described in the previously cited publication of Press et al. The result is an estimate for the pose of the second data set in the coordinate frame of the first data set.

The described refinement and evaluation process is executed using a multiresolution set of Gaussians. Initially, a broad based Gaussian is used to allow influence over large areas, resulting in a coarser alignment, but one which can be reached from a wide range of starting positions. Subsequently, more narrowly tuned Gaussian distributions can be used to refine the pose, while focusing on only nearby data points to derive the pose.

The image data processor next operates to perform a detailed refinement method (step 209) which includes the stages of least squares transformation evaluation (step 210), Powell's method of optimization (step 211), and random transformation perturbation (step 212).

Based on the resulting pose of the interpolated refinement, the pose evaluation process is repeated using a rectified least squares distance measure. Each pose is evaluated by measuring the distance from each transformed data point to the nearest reference surface point (with a cutoff at a predefined maximum distance to guard against outliers or missing data). The pose evaluation is the sum of the squared distances of each data point. Powell's method is again used to find the least-squares pose solution. Here the evaluation function is shown in the following equation:

$$E_2(T) = \sum_i \min\left\{d_{\max}^2, \min_j |Tl_i - m_j|^2\right\} \qquad (2)$$

where $d_{max}$ is a preset maximum distance. The expectation is that this second objective function is more accurate locally, since it is composed of saturated quadratic forms, but it is also prone to getting stuck in local minima.

In order to avoid such local minima, the solution is randomly perturbed and subjected to a repeat of the least squares refinement. The observation is that while the above method always gets very close to the best solution, it can get trapped into local minima in the minimization of E2. Accordingly, this perturbation and refinement process is continued, keeping the new pose if its associated E2 value is better than the current best solution. The process is terminated when the number of such trials that have passed since the E2 value was last improved becomes larger than a predetermined threshold. The final result is a pose, and a measure of the residual deviation of the fit to the reference surface.

While the exemplary embodiment involves using laser scanning to derive one data set, and segmented skin surfaces from MRI or CT to derive the second data set, the method is not restricted to such data inputs. For example, in change detection, the goal is to measure differences between MRI or CT scans taken of the same patient at different times. In this case, the registration technique takes as input two different MRI data sets, and registers sampled points from the same anatomical surface (e.g. the intercranial cavity). The results can then be used to align an MRI scan with the first such scan, to resection the aligned scan so that the slices correspond to the slice planes of the original scan, and then to take image differences between the original slices and the resectioned aligned slices. Such image differences can be used to evaluate changes in structures such as lesions or tumors, for example, to measure the effectiveness of drug or radiation therapy by measuring the change in the size of the structure after treatment.

Figure 3:
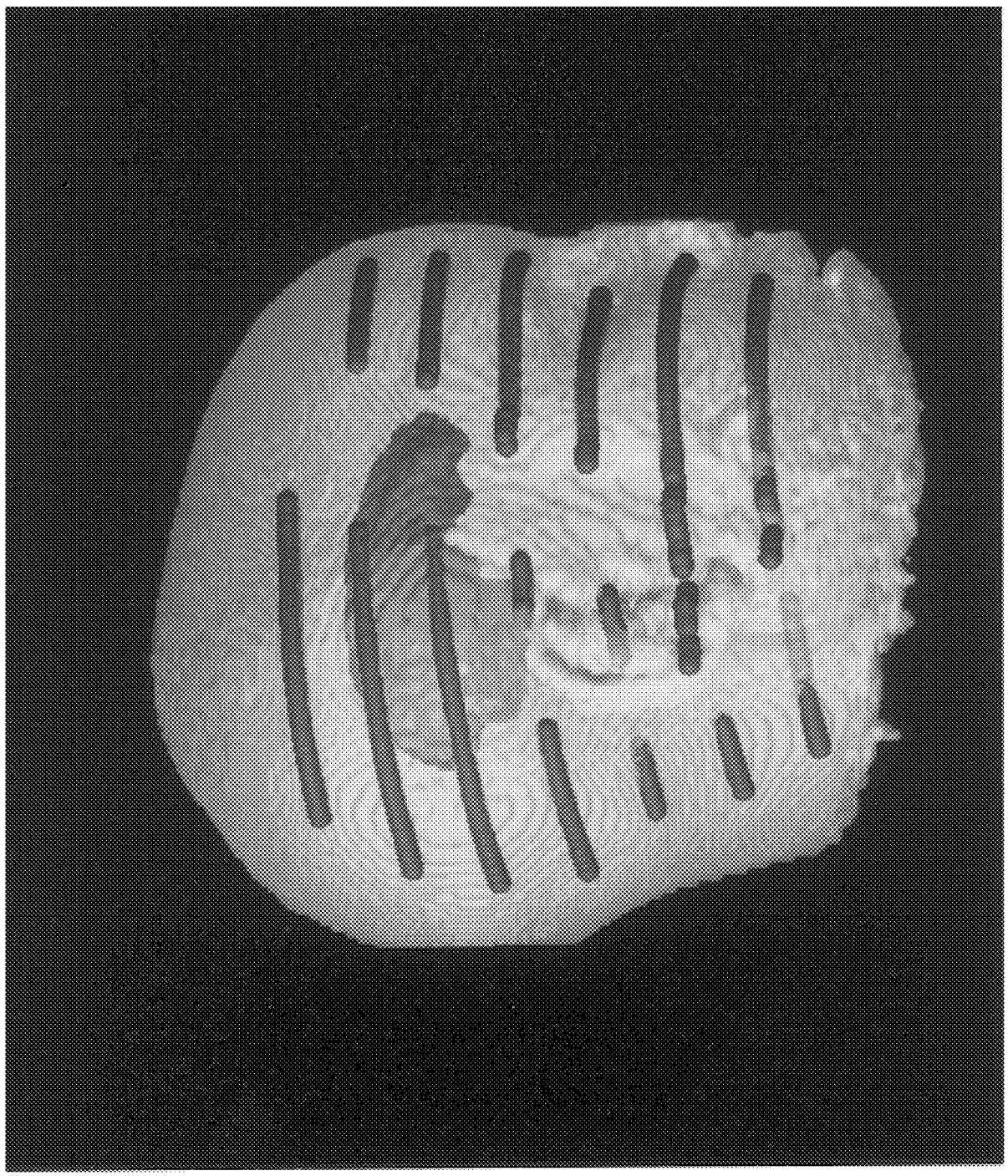
FIG. 3 shows exemplary results of registering laser data derived from laser scan lines of a head to the skin surface segmented from an MRI data set.

Given the output of the registration stage, and the segmented MRI or CT data, the transformation stage (step 213) simply applies the rigid coordinate frame transformation to all of the data, bringing it into the coordinate frame of the laser data. This transformed data set is then passed to the video mixing stage. For purposes of illustration, FIG. 3 shows exemplary results of registering laser data derived from laser scan lines of a head to the skin surface segmented from an MRI data set. The laser scan lines (red curves) are shown overlaid on the MRI skin (shown in white) after the registration process is completed. The anatomical structures segmented from the MRI scan are depicted with a tumor being green and ventricle in blue.

The final stage of the process takes as input a transformed model of the patient's anatomy, (e.g. MRI or CT), where the transformation has brought the model into alignment with the actual position of the patient in the laser coordinate frame, and a video view of the patient taken from the laser camera 110 associated with the laser scanning system. Because the transformed model is now in the coordinate frame of the laser system, which is measured relative to the camera, the image data processor can straightforwardly project the model into the plane of the video image, creating a virtual image of the model. This image can then be mixed with the live video image of the patient taken by the real-time video camera 116, to provide an enhanced visualization.

Figure 4:
FIG. 4 shows exemplary final results of the system of the present invention as a combined video/MRI visualization in which a surgeon is provided with an enhanced visualization view inside of the head of a patient.

For illustrative purposes, FIG. 4 shows exemplary final results of the system 100 as a combined video/MRI visualization in which a surgeon is provided with an enhanced visualization view inside of the head of a patient. The registration transformation computed between the laser and MRI coordinate frames as shown in FIG. 3, directly supports the visualization from the viewpoint of a calibrated camera. The tumor is shown in green and ventricle in blue.

The video mixing can be done for any selected portion of the anatomy of the model. In one embodiment, only the tumor is overlaid on the video image. In this case, the surgeon can use the alignment, as viewed on a video screen, to mark surgical plans on the patient's scalp, e.g. recording the position of the tumor from that viewpoint, marking locations for making the incision to fold back a flap of skin, marking positions for making the craniotomy, etc. In alternative embodiments, the video output can be provided to a head-mounted display device, a surgical microscope having a video overlay feed, or a transparent projection screen.

The registration process described heretofore is also extended to facilitate the tracking of surgical instruments and probes. An exemplary scenario involves the insertion of a rigid instrument into the sinus cavity of a patient. The primary goal of such an insertion, typically, is to achieve removal of material from an interior structure of the patient, without the need for extensive surgical invasion of the patient.

Due to the fact that the surgeon's view is often obstructed by parts of the patient and by the surgeon's hands, it is desirable to provide a type of visual feedback to the surgeon to accommodate viewing the position of the instrument in the patient, thus enhancing the ability to guide further insertions and procedures with the rigid instrument. The process involves registering the three-dimensional anatomical data (MRI, CT, etc.) to the three-dimensional skin surface data, which corresponds to the position of the patient; registering data related to a trackable probe to the three-dimensional skin surface data; and thereafter utilizing the data registration between the probe and the skin surface to provide visualization information to the surgeon.

Figure 5:
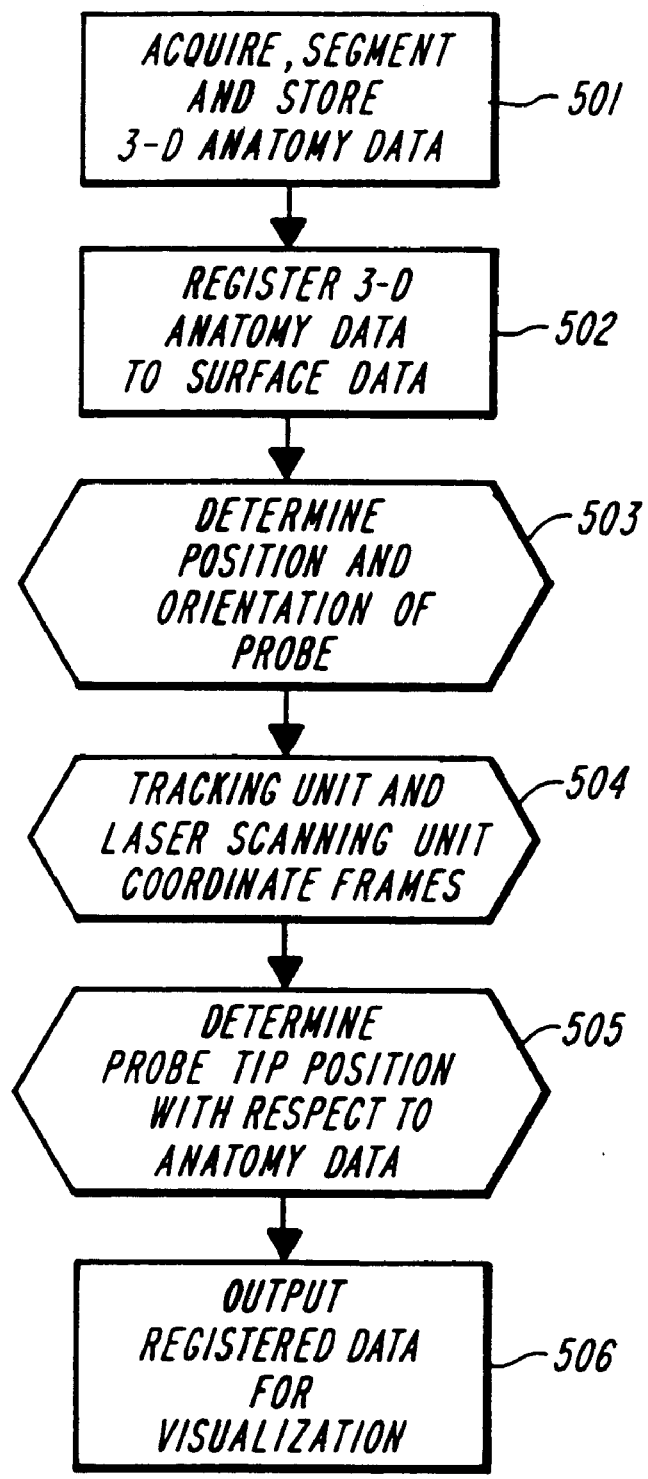
FIG. 5 shows a flowchart of the data registration process in accordance with the present invention incorporating a trackable surgical probe in accordance with the present invention.
Figure 6:
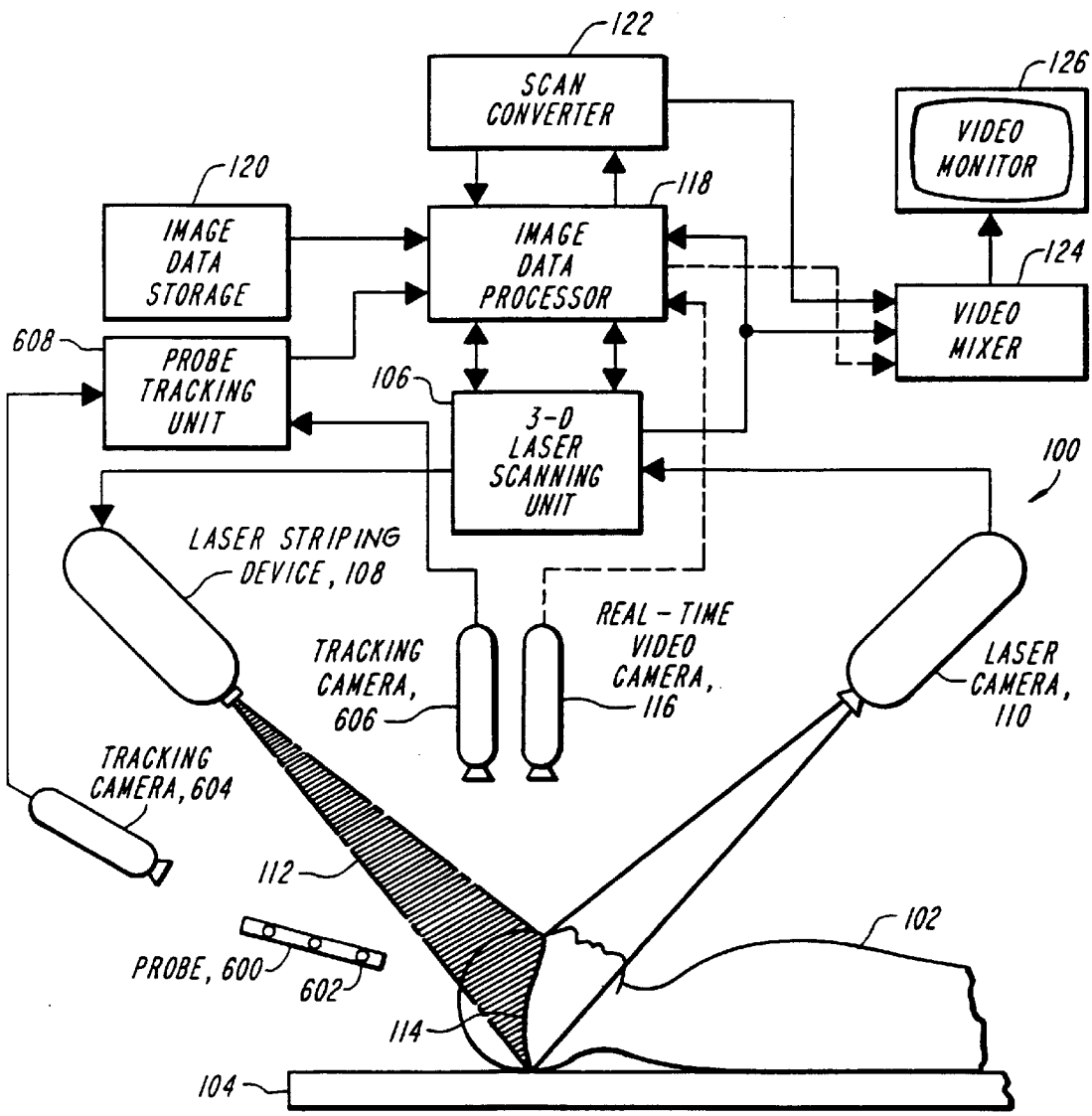
FIG. 6 shows a block diagram of an exemplary image data registration system incorporating a trackable probe.

With reference to FIGS. 5 and 6, an exemplary alternative embodiment of the present invention including data registration and visualization with respect to a trackable probe is presented. FIG. 5 shows a flowchart of the data registration process in accordance with the present invention incorporating a trackable surgical probe in accordance with the present invention. FIG. 6 shows a block diagram of an exemplary image data registration system incorporating a trackable probe.

Initially, (step 501) a medical scan of the patient, e.g. MRI, CT, is acquired and segmented into anatomical structures as previously described. The three-dimensional anatomy image data is stored in storage 120. Thereafter, (step 502) the stored anatomy image data is then registered to the skin surface image data acquired by the laser scanning unit 106 as described in detail with reference to FIGS. 1 and 2.

At this point in the process, the probe 600 is tracked so as to determine both its position and orientation with respect to the patient (step 503). The probe to be tracked is equipped with a set of markers 602 which are preferably positioned at an end of the probe that will remain outside the body cavity. The markers are, for example, visual patterns or infrared light emitting diodes (IR-LEDs). The markers are tracked by a set of tracking cameras 604, 606. The cameras forward the measured positional information of the markers to a probe tracking unit 608, which in turn operates to determine the position and orientation of the probe relative to a coordinate frame associated with the cameras and tracking unit. It will be appreciated by those of skill in the art that a generic system for tracking visual markers is commercially available as the Pixsys Tracking System manufactured by Image Guided Therapy Inc. or the Optotrack Tracking System manufactured by Optotrack Inc.

The coordinate frame utilized by the tracking unit is then calibrated to the coordinate frame of the laser scanning unit 106 (step 504) by the image data processor 118 which initially measures and matches a small set of points from each data set as previously described. Typically this calibration is carried out by measuring a set of points on a calibration object with both the laser and trackable probe.

Figure 7:
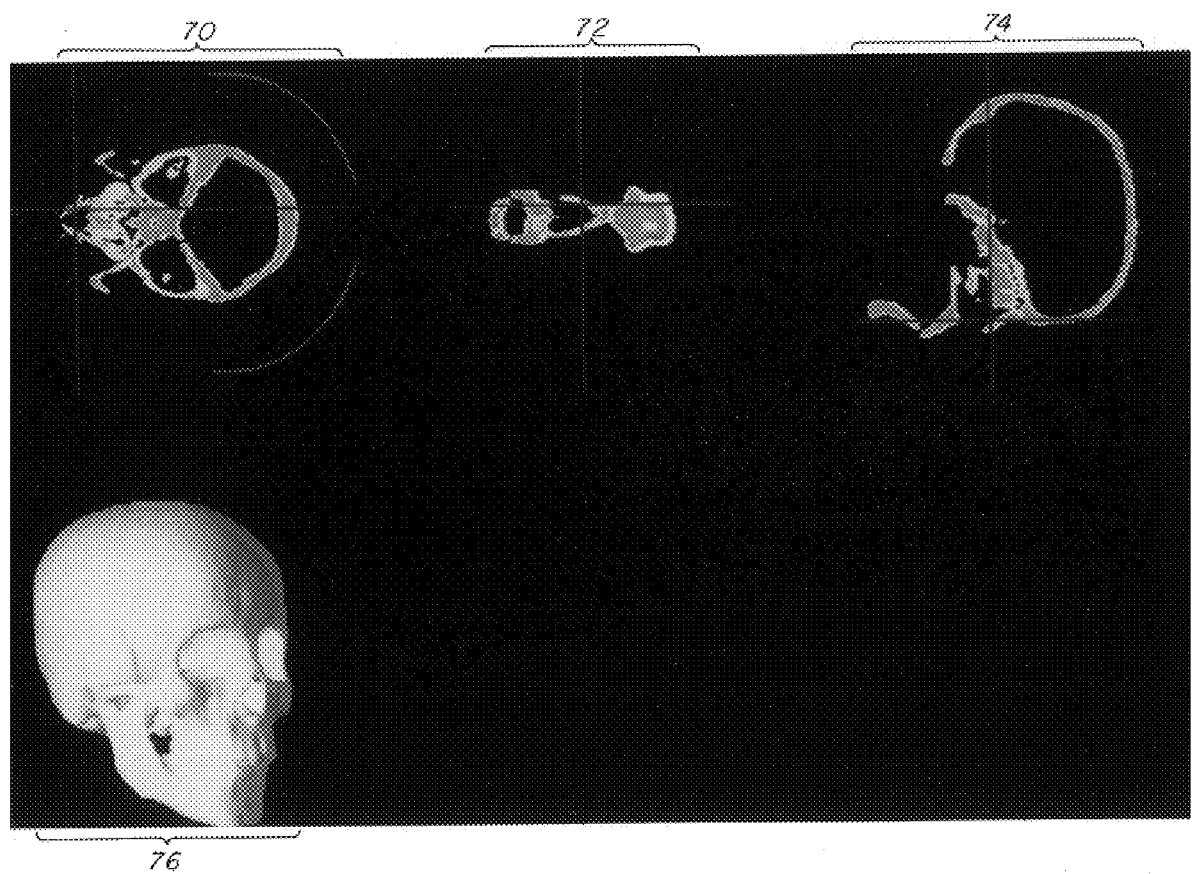
FIG. 7 shows exemplary final results of the system of the present invention as a combined visualization in which a surgeon is provided with an enhanced view inside of the head of a patient and the position of the tip of the trackable probe.

The surgeon will typically proceed by inserting the probe 600 or instrument into the body cavity. The probe tracking unit 608 and tracking cameras 604, 606 observe the markers 602 on the probe, and thereafter computes the position and orientation of the tip of the probe. The tip position is transformed by the image data processor into the coordinate frame of the laser scanning unit or the real-time video camera 116. Due to the data registration technique of the present invention, the transformed positional data of the probe tip is then used to determine the position of the probe tip with respect to the coordinate frame of the anatomy image data (step 505). Accordingly, the registered image data is provided to a visualization output device, for example, the video mixer 124 and video monitor 126, so as to present to the surgeon a viewpoint of where the tip of the probe (which is hidden in the cavity) lies with respect to the full anatomical reconstruction of the patient (step 506). An exemplary visualization output of the present invention is provided in FIG. 7, which illustrates three cross-sectional slices through a full anatomical image data set of a skull, and a view of the full three-dimensional model of the skull with the position of the probe shown as P.

The foregoing description has been set forth to illustrate the invention and is not intended to be limiting. Since modifications of the described embodiments incorporating the spirit and substance of the invention may occur to persons skilled in the art, the scope of the invention should be limited solely with reference to the appended claims and equivalents thereof.

What is claimed is:

1. An image data registration system comprising:
    an image data storage unit for storing a first data set of three-dimensional image data associated with a predetermined portion of an object with reference to a first coordinate frame;
    a first image data acquisition and storage device for obtaining and storing a second data set of three-dimensional image data associated with a surface of said predetermined portion of said object with reference to a second coordinate frame; and
    a second image data acquisition and storage device for obtaining and storing a third data set of three-dimensional image data associated with a movable probe positioned in close proximity to said predetermined portion of said object with reference to a third coordinate frame;
    an image data processor for registering said first, second and third data sets of three-dimensional image data to generate a matched image data set of three-dimensional image data in which said first, second and third coordinate frames are relatively aligned with one another.

2. The system of claim 1, wherein said object is an anatomical body.

3. The system of claim 2, wherein said first data set of three-dimensional image data comprises three-dimensional anatomy image data.

4. The system of claim 3, wherein said first image data acquisition and storage device comprises a surface scanning unit for scanning an outer skin surface of said predetermined portion of the body so as to obtain said second data set of three-dimensional image data.

5. The system of claim 1, wherein said image data processor is operable for selecting a predetermined subset of data points from said third data set.

6. The system of claim 5, wherein said image data processor is further operable for matching said subset of data points to all possible corresponding subsets of data points associated with said second data set which results in a set of hypothesized transformation data sets.

7. The system of claim 6, wherein said image data processor is further operable for sequentially mapping said second data set to each of said hypothesized transformation data sets to form a solution data set, said solution data set representative of a highly accurate transformation of said second data set into the third coordinate frame associated with said third data set.

8. The system of claim 1, wherein said second data acquisition and storage device comprises a probe tracking unit which tracks visual marks associated with said probe so as to obtain said third data set of three-dimensional data.

9. The system of claim 8, wherein said image data processor determines position and orientation of said probe with respect to said first and second coordinate frames.

10. The system of claim 9, wherein said image data processor determines and transforms the position and orientation of a tip of said probe with respect to said first and second coordinate frames.

11. The system of claim 10 further comprising an image output device for producing an output image corresponding to the tip of said probe with respect to said matched image data set.

12. A surgical image registration system comprising:
   a first storage device for storing three-dimensional anatomy image data associated with a predetermined portion of a patient's body with reference to a first coordinate frame;
   a surface scanning unit for scanning the skin surface of said predetermined portion of the patient's body so as to obtain three-dimensional surface image data;
   a second storage device for storing said three-dimensional surface image data with reference to a second coordinate frame;
   a probe tracking unit for tracking visual markers associated with a movable probe positioned in close proximity to said predetermined portion of the patient's body so as to obtain three-dimensional probe image data;
   a third storage device for storing said three-dimensional probe image data with reference to a third coordinate frame; and
   an image data processor operable for registering said three-dimensional anatomy image data, said three-dimensional surface image data and said three-dimensional probe image data to produce a matched image data set of three-dimensional image data in which said first, second and third coordinate frames are relatively aligned with one another.

13. The system of claim 12 further comprising an image output device for producing an output image corresponding to a combination of said matched image data set.

14. The system of claim 13, wherein said image output device comprises a video display monitor.

15. The system of claim 13, wherein said image output device comprises a head-mounted display device.

16. The system of claim 13, wherein said image output device comprises a surgical microscope.

17. The system of claim 13, wherein said image output device comprises a transparent projection screen.

18. The system of claim 12, wherein said three-dimensional anatomy image data comprises prerecorded magnetic resonance imaging (MRI) data.

19. The system of claim 12 wherein said three-dimensional anatomy image data comprises prerecorded computed tomography (CT) data.

20. The system of claim 12, wherein said three-dimensional anatomy image data is segmented into tissue types.

21. The system of claim 12, wherein said surface scanning unit comprises a device for illuminating and reading a sequence of laser lines across the skin surface of said predetermined portion of the patient's body.

22. The system of claim 12, wherein said image data processor is operable for selecting a predetermined subset of data points from said probe image data.

23. The system of claim 22, wherein said image data processor is further operable for matching said subset of data points to all possible corresponding subsets of data points associated with said surface image data which results in a set of hypothesized transformation data sets.

24. The system of claim 23, wherein said image data processor is further operable for sequentially mapping said surface image data to each of said hypothesized transformation data sets to form a solution data set, said solution data set representative of a highly accurate transformation of said surface image data into the third coordinate frame associated with said probe image data.

25. The system of claim 12, wherein said image data processor determines position and orientation of said probe with respect to said first and second coordinate frames.

26. The system of claim 25, wherein said image data processor determines and transforms the position and orientation of the tip of said probe with respect to said first and second coordinate frames.

27. The system of claim 26 further comprising an image output device for producing an output image corresponding to the tip of said probe with respect to said matched image data set.

28. A method of registering three-dimensional image data sets in a surgical imaging system, comprising:
   storing three-dimensional anatomy image data associated with a predetermined portion of a patient's body with reference to a first coordinate frame;
   scanning the skin surface of said predetermined portion of the patient's body so as to obtain three-dimensional surface image data;
   storing said three-dimensional surface image data with reference to a second coordinate frame;
   tracking visual markers associated with a movable probe positioned in close proximity to said predetermined portion of the patient's body so as to obtain three-dimensional probe image data;
   storing said three-dimensional probe image data with reference to a third coordinate frame;
   registering said three-dimensional anatomy data, said three-dimensional surface image data and said three-dimensional probe data to produce a matched image data set of three-dimensional image data in which said first, second and third coordinate frames are relatively aligned with one another; and
   producing an output image corresponding to a combination of said matched image data set of three-dimensional image data.

29. The method of claim 28, wherein said scanning further comprises illuminating and reading a sequence of laser lines across the skin surface of said predetermined portion of the patient's body.

30. The method of claim 28, wherein said registering further comprises selecting a predetermined subset of data points from said surface image data.

31. The method of claim 30, wherein said registering further comprises matching said subset of data points to all possible corresponding subsets of data points associated with said anatomy image data and producing a set of hypothesized transformation data sets.

32. The method of claim 31, wherein said registering further comprises sequentially mapping said anatomy image data to each of said hypothesized transformation data sets to form a solution data set, said solution data set representative of a highly accurate transformation of said anatomy image data into the second coordinate frame associated with said surface image data.

33. The method of claim 32, wherein said sequential mapping further comprises performing a least-squares minimization between said anatomy image data and said surface image data.

34. The method of claim 33, wherein said sequential mapping further comprises randomly perturbing said solution data set and repeating said least-squares minimization in order to avoid local minima and solve for a global minima.

35. The method of claim 28, wherein said registering further comprises selecting a predetermined subset of data points from said probe image data.

36. The method of claim 35, wherein said registering further comprises matching said subset of data points to all possible corresponding subsets of data points associated with said surface image data and producing a set of hypothesized transformation data sets.

37. The method of claim 36, wherein said registering further comprises sequentially mapping said surface image data to each of said hypothesized transformation data sets to form a solution data set, said solution data set representative of a highly accurate transformation of said surface image data into the third coordinate frame associated with said probe image data.

38. The method of claim 37, wherein said sequential mapping further comprises performing a least-squares minimization between said surface image data and said probe image data.

39. The method of claim 38, wherein said sequential mapping further comprises randomly perturbing said solution data set and repeating said least-squares minimization in order to avoid local minima and solve for a global minima.

* * * * *